United States Patent
Mou et al.

(10) Patent No.: US 11,434,212 B2
(45) Date of Patent: Sep. 6, 2022

(54) BICYCLIC COMPOUND AS A CASPASE INHIBITOR

(71) Applicant: CHIA TAI TIANQING PHARMACEUTICAL GROUP CO., LTD., Lianyungang (CN)

(72) Inventors: Jianfeng Mou, Nanjing (CN); Songliang Wu, Nanjing (CN); Haiying He, Nanjing (CN); Fengying Guo, Nanjing (CN); Chuan Wang, Nanjing (CN); Jie Li, Nanjing (CN); Jian Li, Nanjing (CN); Shuhui Chen, Nanjing (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 282 days.

(21) Appl. No.: 16/479,673

(22) PCT Filed: Jan. 23, 2018

(86) PCT No.: PCT/CN2018/073721
§ 371 (c)(1),
(2) Date: Jul. 22, 2019

(87) PCT Pub. No.: WO2018/133870
PCT Pub. Date: Jul. 26, 2018

(65) Prior Publication Data
US 2021/0332019 A1    Oct. 28, 2021

(30) Foreign Application Priority Data
Jan. 23, 2017 (CN) .......................... 201710059063.8

(51) Int. Cl.
| | |
|---|---|
| *C07D 261/18* | (2006.01) |
| *C07D 231/14* | (2006.01) |
| *C07D 233/90* | (2006.01) |
| *C07D 263/34* | (2006.01) |
| *C07D 271/06* | (2006.01) |
| *C07D 277/56* | (2006.01) |

(52) U.S. Cl.
CPC ......... *C07D 261/18* (2013.01); *C07D 231/14* (2013.01); *C07D 233/90* (2013.01); *C07D 263/34* (2013.01); *C07D 271/06* (2013.01); *C07D 277/56* (2013.01)

(58) Field of Classification Search
CPC .................................................. C07D 261/18
See application file for complete search history.

(56) References Cited

FOREIGN PATENT DOCUMENTS

| CN | 1313846 A | 9/2001 |
| CN | 1345332 A | 4/2002 |
| CN | 101573328 A | 11/2009 |
| JP | 2003-506389 A | 2/2003 |
| JP | 2003-516393 A | 5/2003 |
| JP | 2003-534325 A | 11/2003 |
| JP | 2010-509318 A | 3/2010 |
| WO | WO 01/10383 A2 | 2/2001 |
| WO | WO 01/42216 A2 | 6/2001 |
| WO | WO 01/90070 A2 | 11/2001 |
| WO | WO 02/42278 A2 | 5/2002 |
| WO | WO 2003/068242 | 8/2003 |
| WO | WO 2008/056897 A1 | 5/2008 |

OTHER PUBLICATIONS

Olsson, et al. Cell Death and Differentiation (2011) 18, 1441-1449.*
Cancer and Metastasis Reviews (1998), 17(1), 91-106.*
Science (1999), vol. 286, 531-537.*
Cancer [online], [retrieved on Jul. 6, 2007], Retrieved from the internet, URL http://www.nlm.nih.gov/medlineplus/cancer.html>.*
Wannian, Z., "Modern Pharmaceutical Design—Chapter 2: Basic Principles of Drug Design," China Medical Science and Technology Press, pp. 125-126, 347 (2006).
Ueno, H. et al., "Synthesis and structure-activity relationships of oxamyl dipeptide caspase inhibitors developed for the treatment of liver disease," Bioorganic & Medicinal Chemistry Letters 19(1): 199-202 (2008).
International Search Report in International Application No. PCT/CN2018/073721, dated Apr. 28, 2018 (12 pages, w/English translation).
Written Opinion in International Application No. PCT/CN2018/073721, dated Apr. 28, 2018 (10 pages, w/English translation).
Extended European Search Report in European Patent Application No. EP 18741759.7, dated Oct. 23, 2020 (5 pages).

* cited by examiner

*Primary Examiner* — Shawquia Jackson
(74) *Attorney, Agent, or Firm* — Nixon Peabody LLP

(57) ABSTRACT

A compound represented by formula (I), a pharmaceutically acceptable salt or tautomer thereof, and an application of the compound as a caspase inhibitor.

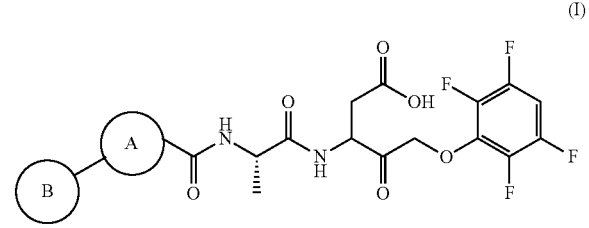

20 Claims, No Drawings

BICYCLIC COMPOUND AS A CASPASE INHIBITOR

REFERENCE TO RELATED APPLICATIONS

This application is a U.S. national stage of PCT/CN2018/073721 filed on Jan. 23, 2018, which claims the benefits of Chinese patent application No. 201710059063.8, filed on Jan. 23, 2017 before the China National Intellectual Property Administration, all the contents of which are incorporated herein by reference in their entireties.

TECHNICAL FIELD

The present application relates to a new class of compounds and pharmaceutically acceptable salts of the same as caspase inhibitor, and further relates to a pharmaceutical composition containing these compounds and a method for using such pharmaceutical compositions.

BACKGROUND

The control of the number of mammalian cell depends on the balance between reproduction and death of the cell to some extent. Necrotic cell death is one of the forms of cell death, characterized by pathological cell death caused by cell damage or injury. Necrotic cell death is harmful to tissues, such as, leading to inflammation. In contrast, another physiological form of cell death occurs in an orderly, controlled form. This orderly, controlled form of cell death is called as apoptotic cell death (Barr, et al., Bio/Technology, 12: 487-497, 1994; Steller, et al., 267: 1445-1449, 1995). Through this programmed manner of apoptotic cell death, an organism eliminates unwanted cells (activity and presence of the cells are no longer needed) without damaging other tissues. Therefore, apoptotic cell death is an extremely important physiological process to maintain the normal development and dynamic equilibrium of an organism. There are many factors that can cause apoptotic cell death. Among them, the most important factor is a class of proteases called caspase (cysteine aspartate-specific protease, and 14 caspase proteases are known). Caspase is a type of cysteine protease, and many important proteins in cells are its substrate. The process of apoptotic cell death includes that cell debris formed by decomposing cells under the action of a caspase enzyme is absorbed by other cells, or eliminated by macrophages and the like without causing inflammation, etc.

SUMMARY OF THE INVENTION

The present application provides a compound represented by formula (I), a pharmaceutically acceptable salt or tautomer thereof,

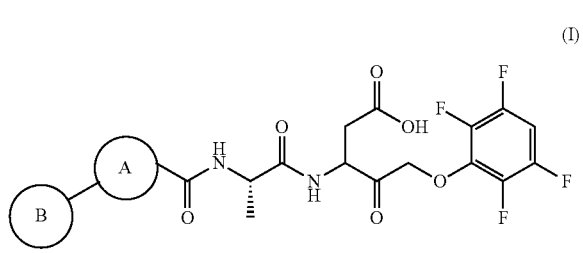

(I)

wherein,
ring A is selected from a 5- or 6-membered heteroaryl group, which is optionally substituted with R;
ring B is selected from phenyl or $C_{3-6}$ cycloalkyl, which is optionally substituted with R;
R is selected from halogen, OH, $NH_2$, or a $C_{1-3}$ alkyl group optionally substituted with 1, 2 or 3 $R^1$;
$R^1$ is selected from F, Cl, Br, I, OH, $NH_2$, $NH(CH_3)$ or $N(CH_3)_2$.

In some embodiments of the present application, a heteroatom of ring A is independently selected from O, S or N.

In some embodiments of the present application, number of the heteroatom of ring A is selected from 1, 2 or 3.

In some embodiments of the present application, the above ring A is selected from oxazolyl, isoxazolyl, imidazolyl, thiazolyl, 1,2,4-oxadiazolyl, 1,3,4-oxadiazolyl or pyrazolyl.

In some embodiments of the present application, the above ring A is selected from

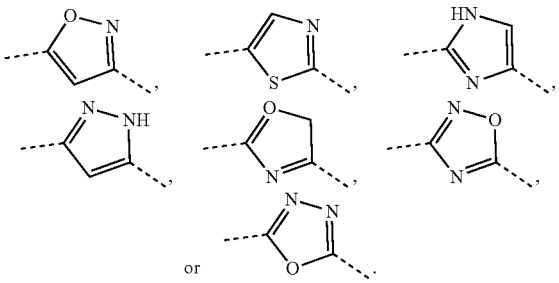

or

In some embodiments of the present application, the above ring B is selected from phenyl or cyclohexyl, which is optionally substituted with R.

In some embodiments of the present application, the above R is selected from F, Cl, Br, I, OH, $NH_2$, or Me or Et optionally substituted with 1, 2 or 3 $R^1$. In some embodiments of the present application, the above $R^1$ is selected from F, Cl or $NH_2$.

In some embodiments of the present application, the above R is selected from F, Cl, Br, I, OH, $NH_2$, or Me or Et optionally substituted with 1, 2 or 3 F.

In some embodiments of the present application, the above R is selected from F, Cl, Br, I, OH, $NH_2$ or $CF_3$.

In some embodiments of the present application, the above ring B is selected from

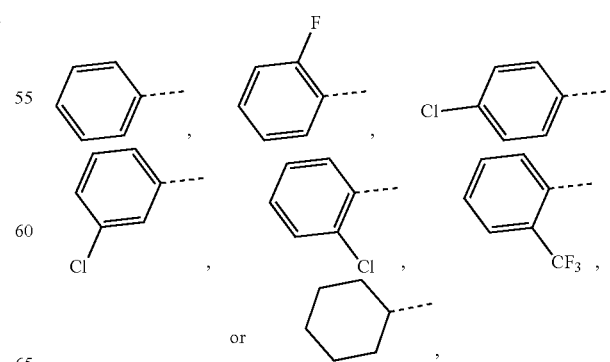

or

In some embodiments of the present application,

[structure: B-A with dashed bond]

is selected from

[phenyl-isoxazole structure],

[phenyl-isoxazole structure],

[phenyl-thiazole structure],

[phenyl-imidazole (HN) structure],

[phenyl-pyrazole (NH) structure],

[phenyl-oxazole structure],

[phenyl-1,2,4-oxadiazole structure],

[phenyl-1,3,4-oxadiazole structure],

[phenyl-1,2,4-oxadiazole structure], or

[cyclohexyl-isoxazole structure], and ring B is optionally substituted with R.

In some embodiments of the present application,

[structure: B-A with dashed bond]

is selected from

[R-phenyl-isoxazole structure],

[R-phenyl-isoxazole structure],

[R-phenyl-thiazole structure],

[R-phenyl-imidazole (HN) structure],

[R-phenyl-pyrazole (NH) structure],

[R-phenyl-oxazole structure],

[R-phenyl-1,2,4-oxadiazole structure],

[R-phenyl-1,3,4-oxadiazole structure],

[R-phenyl-1,2,4-oxadiazole structure], or

[R-cyclohexyl-isoxazole structure],

In some embodiments of the present application,

[structure: B-A with dashed bond]

is selected from

[2-R-phenyl-isoxazole structure],

[3-R-phenyl-isoxazole structure],

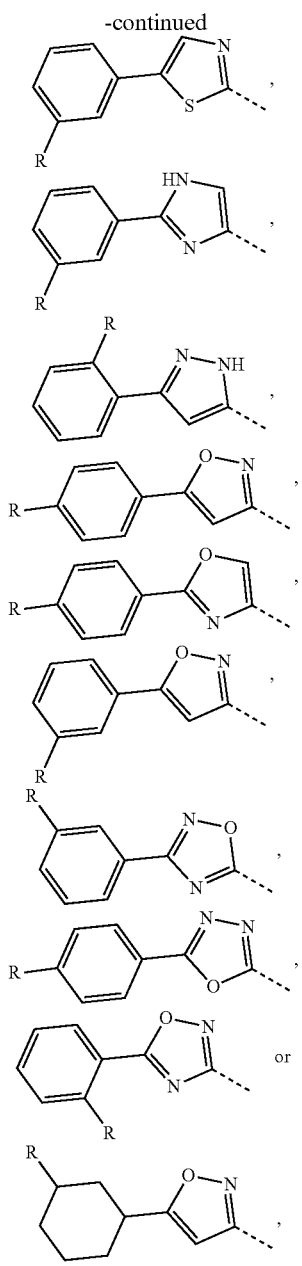
In some embodiments of the present application,
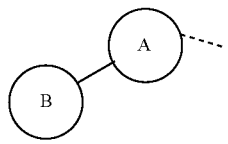 is 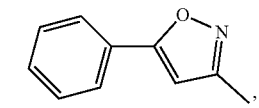,
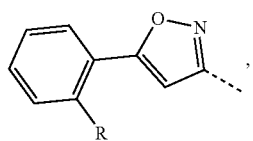
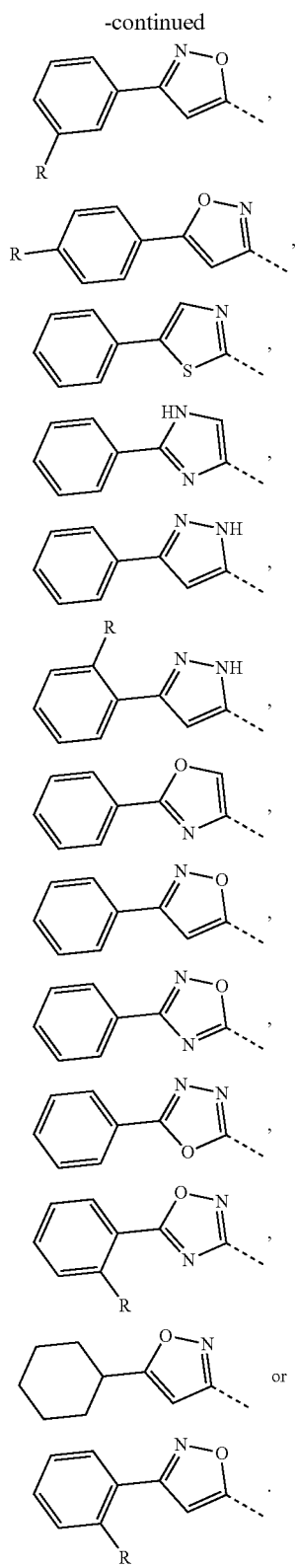
In some embodiments, the compound of formula (I) of the present application is selected from a compound of formula (II),

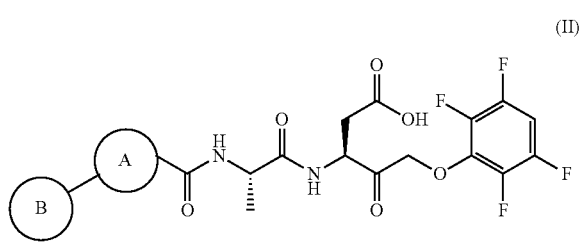
(II)
wherein ring A and ring B are as defined above.
In some embodiments, the compound of formula (I) of the present application is selected from:
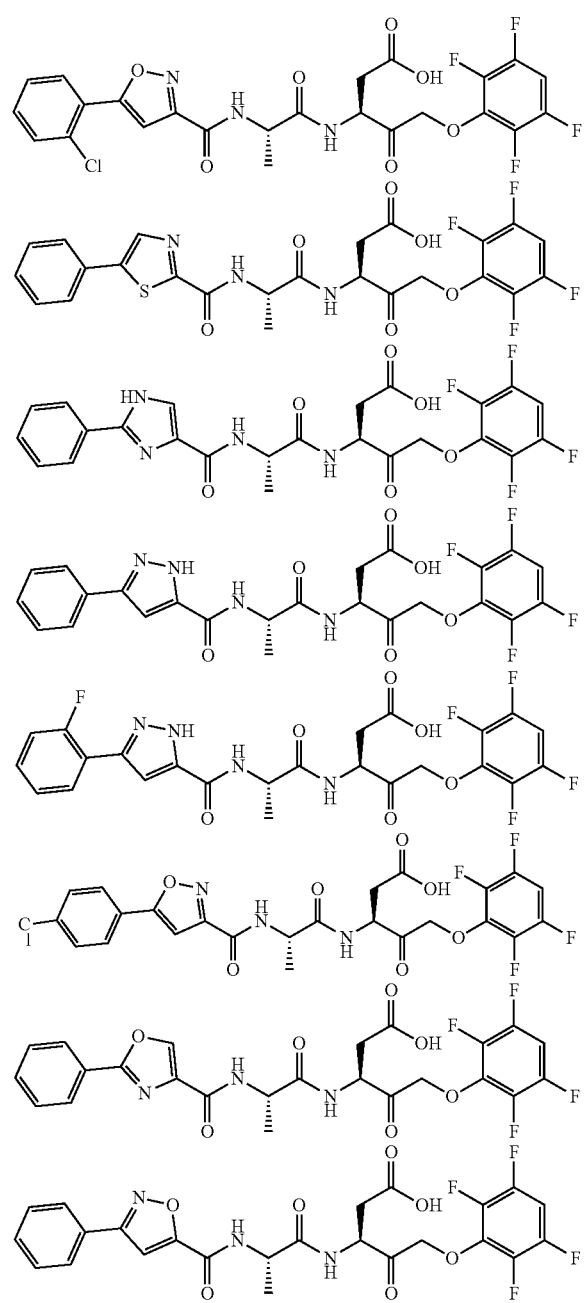
Another object of the present application is to provide a pharmaceutical composition comprising a therapeutically effective amount of the compound of formula (I) or a pharmaceutically acceptable salt thereof, and a pharmaceutically acceptable carrier. Another object of the present application is to provide use of the compound of formula (I) or the pharmaceutically acceptable salt thereof, or the pharmaceutical composition as described above in preparation of a medicament for treating caspase receptor related diseases.

Another object of the present application is to provide a method of treating caspase receptor related diseases in a mammal, comprising administering a therapeutically effective amount of the compound of formula (I) or the pharmaceutically acceptable salt thereof, or the pharmaceutical composition of the same to the mammal (preferably human) in need thereof.

Another object of the present application is to provide a compound of formula (I) or a pharmaceutically acceptable salt thereof for use in preventing or treating caspase receptor related diseases.

Definition and Description

Unless otherwise specified, the following terms and phrases as used herein are intended to have the following meanings. A particular term or phrase should not be considered to be indefinite or unclear in the absence of a specific definition, but should be interpreted as its ordinary meanings. When a trade name appears herein, it is intended to refer to the corresponding commodity or active ingredient thereof.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

The term "pharmaceutically acceptable salt" refers to salt(s) of the compound of the present application, which is prepared from the compound with specific substituents found in the present application and a relatively non-toxic acid or base. When the compound of the present invention contains relatively acidic functional groups, the base addition salts thereof can be obtained by contacting the neutral form of such compound with a sufficient amount of base in a pure solution or a suitable inert solvent. When the compound of the present invention contains relatively basic functional groups, the acid addition salts thereof can be obtained by contacting the neutral form of such compound with a sufficient amount of acid in a pure solution or suitable inert solvent. Certain specific compounds of the present application contain basic and acidic functional groups, and thus can be converted to any base or acid addition salts.

Preferably, the salt is contacted with a base or acid in a conventional manner, and the parent compound is separated, thereby regenerating the neutral form of the compound.

The pharmaceutically acceptable salt of the present application can be synthesized from a parent compound containing an acidic functional group or a basic functional group via conventional chemical methods. In general, such a salt is prepared by a method of reacting these compounds in the form of free acid or base with a stoichiometric amount of a suitable base or acid in water or an organic solvent or a mixture thereof. Generally, the organic solvent is preferably a nonaqueous medium, such as ether, ethyl acetate, ethanol, isopropanol or acetonitrile.

In addition to the form of salt, the compound provided by the present application also includes the form of prodrug. Prodrug of the compound described herein readily undergoes chemical changes under physiological conditions, to be converted to the compound of the present application. In addition, prodrug can be converted to the compound of the present application by chemical or biochemical methods in an in vivo environment.

Certain compounds of the present application may exist in a non-solvated or solvated form, including a hydrated form. In general, the solvated form is equivalent to the non-solvated form, both of which are encompassed within the scope of the present application.

Certain compounds of the present application may have an asymmetric carbon atom (optical center) or a double bond. Racemates, diastereomers, geometric isomers, and individual isomers are all included within the scope of the present application.

Unless otherwise stated, solid wedge bond and dashed wedge bond ( ⟋ and ⋯⋯ ) are used to indicate the absolute configuration of a stereocenter, and the wavy line ⌇ is used to indicate the solid wedge bond and dashed wedge bond ( ⟋ and ⋯⋯ ). When the compounds described herein contain olefinic double bonds or other geometric asymmetrical centers, unless otherwise specified, they include E, Z geometric isomers. Likewise, all tautomeric forms are included within the scope of the present application.

The compounds of the present application may exist in specific geometric or stereoisomeric forms. All such compounds envisaged by the present application include cis and trans isomers, (−)- and (+)-enantiomers, (R)- and (S)-enantiomers, diastereomers, (D)-isomers, (L)-isomers, and racemic mixtures and other mixtures thereof, such as enantiomers or diastereomers enriched mixtures, all of which fall within the scope of the present application. Other asymmetric carbon atoms may be present in the substituents such as alkyl. All these isomers and their mixtures are included in the scope of the present application.

The optically active (R)- and (S)-isomers as well as the D and L isomers can be prepared by chiral synthesis or chiral reagents or other conventional techniques. If an enantiomer of a certain compound of the present application is desired, it may be prepared by asymmetric synthesis, or by derivatization with a chiral auxiliary, wherein the resulting diastereomeric mixture is separated and the ancillary group is cleaved to provide the pure desired enantiomers. Alternatively, when a molecule contains a basic functional group (such as an amino) or an acidic functional group (such as a carboxyl), it forms a salt of diastereomer with a suitable optically active acid or base, and then a diastereomer resolution is performed by conventional methods well known in the art, followed by recovering to give pure enantiomers. In addition, the separation of the enantiomers and diastereomers is generally accomplished by the use of chromatography adopting a chiral stationary phase, and optionally in combination with chemical derivatization method (e.g., forming carbamates from amines).

The compound of the present application may contain non-natural proportions of atomic isotopes on one or more atoms which constitute the compound. For example, the compound may be labeled with a radioisotope, such as tritium ($^3$H), iodine-125 ($^{125}$I) or C-14 ($^{14}$C). Any isotopic composition transformations of the compound of the present application, whether are radioactive or not, are included in the scope of the present application.

The term "pharmaceutically acceptable carrier" refers to any formulation or carrier medium capable of delivering an effective amount of the active substance of the present application, without interfering with the biological activity of the active substance and having no toxic side effects on the host or patient. Representative carriers include water, oils, vegetables and minerals, cream bases, lotion bases, ointment bases, etc. These bases include suspensions, tackifiers, transdermal enhancers, etc. Their formulations are well known to the skilled in the cosmetic field or topical drug field. Other information about carriers can refer to Remington: The Science and Practice of Pharmacy, 21$^{st}$ Ed., Lippincott, Williams & Wilkins (2005), the contents of which are incorporated herein by reference.

The term "excipient" generally refers to the carrier, diluent and/or medium which is required to formulate an effective pharmaceutical composition.

With respect to a drug or a pharmacologically active agent, the term "effective amount" or "therapeutically effective amount" refers to a sufficient amount of a drug or agent that is non-toxic but can achieve the desired effect. For an oral dosage form of the present application, the "effective amount" of one active substance in a composition refers to the amount required to achieve the desired effect when used in combination with another active substance in the composition. The determination of the effective amount varies with each individual, depending on the age and general condition of the subject, as well as the specific active substance. The appropriate effective amount in each case can be determined by the skilled in the art according to routine experiments.

The term "active ingredient", "therapeutic agent", "active substance" or "active agent" refers to a chemical entity that can effectively treat target disorders, diseases or conditions.

The term "optional" or "optionally" means that the subsequently described event or condition may occur, but does not have to occur, and that the description includes instances in which the event or condition occurs and instances in which the event or condition does not occur.

The term "substituted" means that any one or more hydrogens on a specific atom is replaced with a substituent, including variants of hydrogen and heavy hydrogen, provided that the valence of the specific atom is normal and the substituted compound is stable. When the substituent is a ketone group (i.e., =O), it means that two hydrogen atoms are substituted, and the keto-substitution will not occur on an aromatic group. The term "optionally substituted" means that it may be substituted or not, and unless otherwise specified, the species and numbers of substituents may be arbitrary provided that it is chemically achievable.

As used herein, $C_{m-n}$ means that this moiety has m to n carbon atoms. For example, "$C_{3-10}$ cycloalkyl" means that the cycloalkyl has 3 to 10 carbon atoms. A numerical range herein refers to each integer in the given range. For example, "$C_{1-10}$" means that the group may have 1, 2, 3, 4, 5, 6, 7, 8, 9 or 10 carbon atoms.

When any variable (e.g., R) occurs more than one time in constituent or structure of a compound, its definition is independent in each case. Thus, for example, if a group is showed to be substituted with 0-2 R, said group may be optionally substituted with up to two R, and R in each case has independent options. In addition, a combination of substituents and/or variants thereof is allowed only if such combination results in stable compounds.

When a substituent is vacant, it means that the substituent does not exist. For example, when X is vacant in A-X, the structure is actually A.

When a substituent may be linked to one or more atoms on one ring, the substituent may be bonded to any atom on the ring, for example, a structural unit

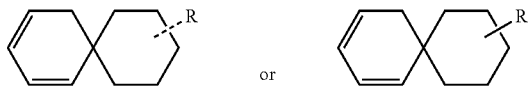

means that any position on the cyclohexyl or cyclohexadiene may be substituted with substituent R. When it is not indicated by which atom the listed substituent is linked to the substituted group, such a substituent may be bonded through any atom thereof, for example, a pyridyl group as a substituent may be bonded to the substituted group through any carbon atom on the pyridyl ring. When the linking direction of the listed linking group is not indicated, the linking direction is arbitrary, for example, when the linking group L in

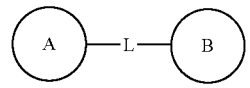

is -M-W-, -M-W- can link ring A to ring B in the direction identical to the reading order from left to right to form

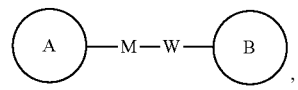

or link ring A to ring B in the direction opposite to the reading order from left to right to form

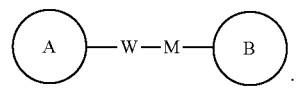

A combination of linking groups, substituents and/or variants thereof is a owed only if such a combination results in stable compounds.

Unless otherwise specified, the term "hetero" refers to a heteroatom or a heteroatomic group (i.e., an atomic group containing a heteroatom), including an atom except for carbon (C) and hydrogen (H), and an atomic group containing these heteroatoms, for example including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and —C(=O)N(H)—, —N(H)—, —C(=NH)—, —S(=O)$_2$N(H)— or —S(=O)N(H)— which is optionally substituted.

Unless otherwise specified, the term "heterocycle" or "heterocyclyl" refers to a stable mono-, bi-, or tri-cyclic ring containing a heteroatom or heteroatomic group, which may be saturated, partially unsaturated, or unsaturated (aromatic), and they contain carbon atoms and 1, 2, 3, or 4 cyclic heteroatoms independently selected from N, O, and S, wherein any of the above heterocycles may be fused to a phenyl ring to form a bicyclic ring. The nitrogen and sulfur heteroatoms may be optionally oxidized (i.e., NO and S(O)$_p$, p is 1 or 2). The nitrogen atom may be substituted or unsubstituted (i.e., N or NR, wherein R is H or other substituents as already defined herein). The heterocyclic ring can be attached to the pendant groups of any heteroatom or carbon atom to form a stable structure. The heterocyclic rings described herein may be substituted on carbon or nitrogen atoms if the resulting compound is stable. N atom in the heterocycle is optionally quaternized. It is preferred that when the total number of S and O atoms in the heterocycle exceeds 1, these heteroatoms are not adjacent to each another. It is preferred that the total number of S and O atoms in the heterocycle is not more than 1.

The term "aromatic heterocyclic group" or "heteroaryl" refers to a stable 5-, 6- or 7-membered monocyclic or bicyclic, or 7-, 8-, 9- or 10-membered bicyclic heterocyclyl aromatic ring, which contains carbon atoms and 1, 2, 3, or 4 cyclic heteroatoms independently selected from N, O, and S. The nitrogen atom may be substituted or unsubstituted (i.e., N or NR, wherein R is H or other substituents as already defined herein). The nitrogen and sulfur heteroatoms may be optionally oxidized (i.e., NO and $S(O)_p$, and p is 1 or 2). It should be noted that the total number of S and O atoms in the aromatic heterocycle is not more than 1. Bridged ring is also included in the definition of heterocycle. A bridged ring is formed when one or more atoms (i.e., C, O, N, or S) link two non-adjacent carbon or nitrogen atoms. Preferred bridged rings include, but are not limited to, one carbon atom, two carbon atoms, one nitrogen atom, two nitrogen atoms, and one carbon-nitrogen group. It should be noted that a bridge always converts a monocyclic ring into a tricyclic ring. In a bridged ring, substituents on the ring may also be present on the bridge.

Unless otherwise specified, the term "hydrocarbyl" or specific term thereof (such as alkyl, alkenyl, alkynyl, aryl, etc.) per se or as part of another substituent means a straight, branched or cyclic hydrocarbon atomic group or a combination thereof, which may be fully saturated (such as an alkyl group), a mono- or a poly-unsaturated (such as an alkenyl group, an alkynyl group, an aryl group), may be monosubstituted or polysubstituted, and may be monovalent (such as methyl), divalent (such as methylene) or polyvalent (such as methine), may include divalent or multivalent atomic group, and has a specified number of carbon atoms (e.g., $C_1$-$C_{12}$ represents 1 to 12 carbons, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). "Hydrocarbyl" includes, but is not limited to, aliphatic hydrocarbyl including chain and cyclic hydrocarbyl, including but not limited to alkyl, alkenyl, alkynyl; and aromatic hydrocarbyl including but not limited to 6-12 aromatic hydrocarbyl, such as phenyl, naphthyl or the like. In some examples, the term "hydrocarbyl" means a straight or branched chain atomic group or a combination thereof, which may be fully saturated, mono- or poly-unsaturated, and may include divalent and multivalent atomic group. Examples of saturated hydrocarbon atomic group include, but are not limited to, methyl, ethyl, n-propyl, isopropyl, n-butyl, t-butyl, isobutyl, sec-butyl, cyclohexyl, (cyclohexyl)methyl, cyclopropylmethyl, and homologue or isomer of an atomic group such as n-pentyl, n-hexyl, n-heptyl or n-octyl. The unsaturated hydrocarbon group has one or more double or triple bonds, and examples thereof include, but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and higher homologues and isomers thereof.

Unless otherwise specified, the term "alkyl" is used to represent a straight or branched saturated hydrocarbon group, which may be monosubstituted (e.g., —$CH_2F$) or polysubstituted (e.g., —$CF_3$), and may be monovalent (e.g., methyl), divalent (such as methylene) or polyvalent (such as methine). Examples of the alkyl group include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl) and the like. Unless otherwise specified, the term "cycloalkyl" includes any stable cyclic or polycyclic hydrocarbon group, any carbon atom of which is saturated, which may be monosubstituted or polysubstituted, and may be monovalent, divalent or polyvalent. Examples of such cycloalkyl groups include, but are not limited to, cyclopropyl, norbornyl, [2.2.2]bicyclooctyl, [4.4.0]bicyclodecyl, and the like.

Unless otherwise specified, the term "halo/halogenated" or "halogen" per se or as part of another substituent represents fluorine, chlorine, bromine or iodine atom.

The compound of the present application may be prepared by various synthesis methods well known to the skilled in the art, including the specific embodiments listed below, the embodiments formed by combining the specific embodiments with other chemical synthesis methods, and equivalent alternatives well known to the skilled in the art, and the preferred embodiments include, but are not limited to, the Examples of the present application.

Solvents used in the present application are commercially available. The following abbreviations are used in the present application: eq represents equivalent; NMM represents N-methylmorpholine; DMSO represents dimethyl sulfoxide; HOBt represents 1-hydroxybenzotriazole; EDCl represents 1-ethyl-(3-dimethylaminopropyl)carbodiimide hydrochloride; TEMPO represents tetramethylpiperidine nitroxide; $T_3P$ represents propylphosphoric anhydride; DIPEA represents N,N-diisopropylethylamine.

The compounds are named manually or via the ChemDraw® software, and the supplier's catalog names are used for the commercially available compounds.

EXAMPLES

The present application is described in detail below by way of examples, but is not intended to be construed as limitation. The present application has been described in detail herein, and the specific embodiments thereof are disclosed. Various changes and modifications made to the embodiments of the present application will be apparent to persons skilled in the art, without departing from the spirit and scope of the present application.

Preparation Example 1: Preparation of Compound 1-a

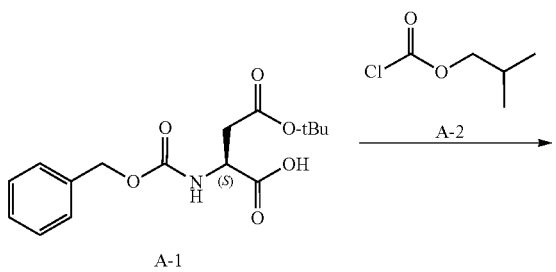

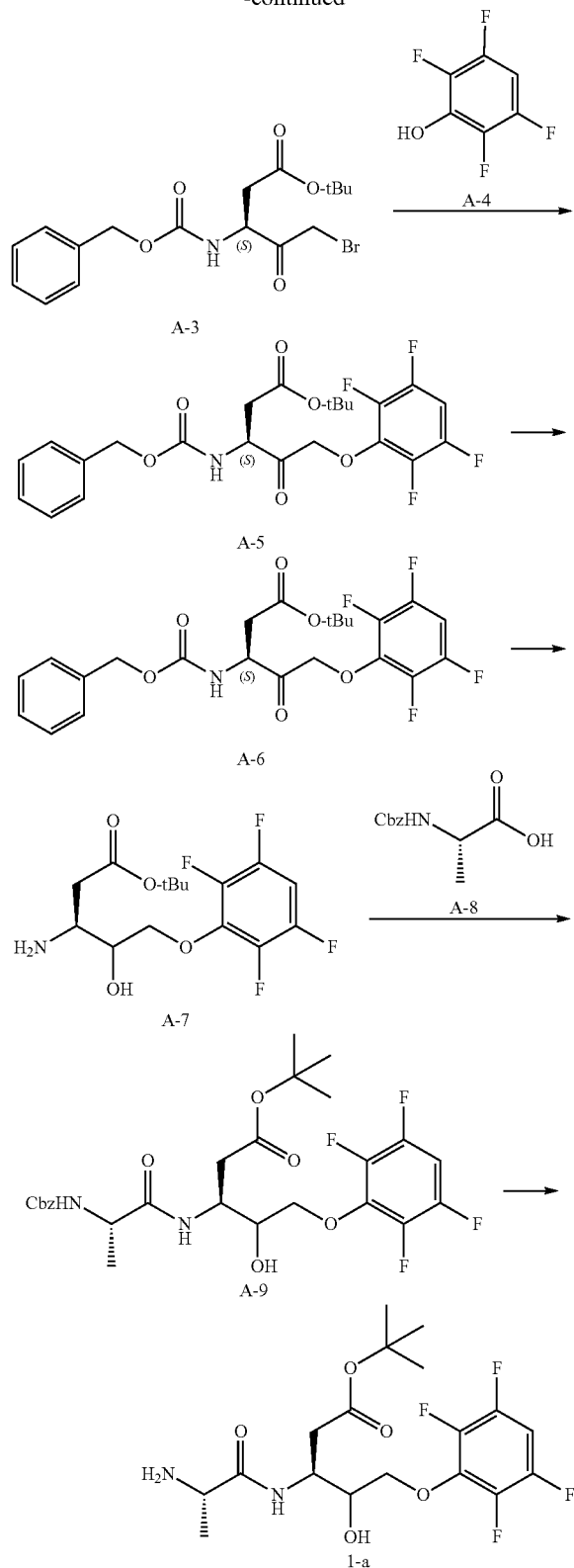

protection of nitrogen at −10° C. Compound A-2 (19.01 g, 139.17 mmol, 18.28 mL, 1.50 eq) was slowly added dropwise thereto, and stirred for 40 min while maintaining the temperature at −10° C. The reaction mixture was filtered, and the filter cake was washed with tetrahydrofuran (200 mL). The combined filtrate was poured into a three-necked flask and kept at the temperature of 0° C. A $CH_2N_2$-diethyl ether solution (370 mL) was added into the flask under the protection of nitrogen, further stirred at 0° C. for 20 minutes, followed by being heated to 20° C. and stirred for another 2 hours. The reaction mixture was then further cooled to 0° C. and treated with HBr (30 mL, 35% acetic acid solution), and then the mixture was stirred at 0° C. for 15 min, followed by being heated to 20° C. and stirred for another 45 min. After the reaction was completed, the reaction mixture was extracted by using ethyl acetate (500 mL) and water (400 mL), and separated. The organic phase was further washed with water (400 mL), saturated sodium bicarbonate solution (400 mL) and saturated saline (400 mL). It was dried over anhydrous sodium sulfate and then concentrated to give a crude product, which was purified by column chromatography to give a colorless oily compound A-3 (30.00 g, yield: 76%).

Step 2: Synthesis of Compound A-5

Compound A-3 (25.00 g, 62.46 mmol, 1.00 eq) and A-4 (12.45 g, 74.95 mmol, 1.20 eq) were dissolved in DMF (350.00 mL). KF (14.52 g, 249.84 mmol, 5.85 mL, 4.00 eq) was added thereto under the protection of nitrogen, and then the reaction was stirred at 20° C. for 15 hours. After the reaction was completed, 500 mL of ethyl acetate was added thereto, and it was washed with saturated sodium bicarbonate solution (350 mL), water (350 mL) and saturated saline (350 mL). The organic phase was dried over anhydrous sodium sulfate, and concentrated to give crude product, which was purified by column chromatography (petroleum ether:ethyl acetate=1:0-3:1) to give compound A-5 (18.00 g, yield: 56%).

Step 3: Synthesis of Compound A-6

Compound A-5 (9.50 g, 19.57 mmol, 1.00 eq) was added into a mixed solvent of methanol (30.00 mL) and tetrahydrofuran (30.00 mL), and then sodium borohydride (2.96 g, 78.28 mmol, 4.00 eq) was added thereto while maintaining the temperature at 0° C., and after the addition was completed, the reaction mixture was stirred at 25° C. for 1 hour. After the reaction was completed, the reaction mixture was added into water (200 mL), and $NH_4Cl$ (200 mL, aq, 10%) was added thereto, and then extracted with ethyl acetate (500 mL*3). The combined organic phase was washed with water (500 mL) and saline (500 mL), dried over anhydrous sodium sulfate, and filtered to give a colorless oily compound A-6 (9.00 g, crude), which was directly used in the next reaction without purification.

Step 4: Synthesis of Compound A-7

Compound A-6 (9.00 g, 18.46 mmol, 1.00 eq) was dissolved in methanol (500.00 mL), and Pd—C (10%, 2.5 g) was added thereto. The mixture was replaced 3 times with hydrogen and maintained at a pressure of 15 psi, and the mixture was stirred for 4 hours while maintaining the temperature at 25° C. After the reaction was completed, filtration and concentration was performed to give a yellow oily compound A-7 (6.10 g, crude), which was directly used in the next reaction without purification.

Step 5: Synthesis of Compound A-9

Compound A-7 (6.10 g, 17.2 mmol, 1.00 eq) and compound A-8 (3.85 g, 17.2 mmol, 1.00 eq) were dissolved in ethyl acetate solution (100 mL), and then $T_3P$ (16.42 g, 25.8 mmol, 1.50 eq, 50% ethyl acetate solution) and DIPEA (4.44

Step 1: Synthesis of Compound A-3

Compound A-1 (30.00 g, 92.78 mmol, 1.00 eq) and 4-methylmorpholine (15.02 g, 148.45 mmol, 16.33 mL, 1.60 eq) were dissolved in tetrahydrofuran (468 mL) under the g, 34.4 mmol, 2.0 eq) were successively added thereto, and stirred at 25° C. for 4 hours. The reaction solution was added with water (50 mL) for quenching and separation. The organic phase was washed once with saturated sodium bicarbonate solution (50 mL), water (50 mL) and saturated saline (50 mL), respectively. The organic phase was dried over anhydrous sodium sulfate and concentrated to give a crude product. The crude product was purified by column chromatography (ethyl acetate:petroleum ether=1:20-1:2) to give the product, compound A-9 (3.50 g, yield: 36.5%); LCMS m/z=581.2 [M+Na]+.

Step 6: Synthesis of Compound 1-a

Compound A-9 (3.30 g, 5.91 mmol, 1.00 eq) was dissolved in a mixed solvent of methanol (33.0 mL) and THE (33.0 mL), and Pd—C (10%, 330 mg) was added thereto. The mixture was replaced three times with hydrogen and maintained at a pressure of 15 psi, and the mixture was stirred for 2 hours while maintaining the temperature at 25° C. After the reaction was completed, filtration and concentration was performed to give yellow oily compound A (2.18 g, 4.50 mmol, yield: 76.2%), which was directly used in the next reaction without purification; LCMS m/z=425.2 [M+H]$^+$.

Preparation Example 2: Preparation of Compound 1-e (Referring to the Preparation Route of Compound 1-a, Replacing Compound A-1 with the Chiral Enantiomer Thereof)

| Compound No. | Structure | MS(m/z) [M + H]$^+$ |
|---|---|---|
| 1-e | 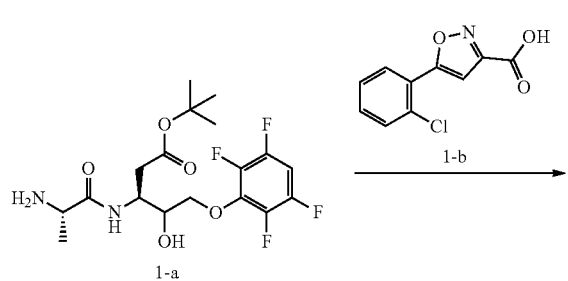 | 425.2 |

Example 1: (S)-3-((S)-2-(5-(2-chlorophenyl)isoxazol-3-carboxamido) propionamido)-4-oxo-5-(2,3,5,6-tetrafluorophenoxy)pentanoic Acid (Compound 1)

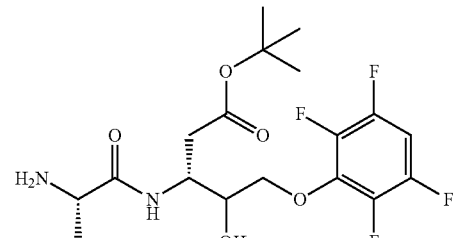

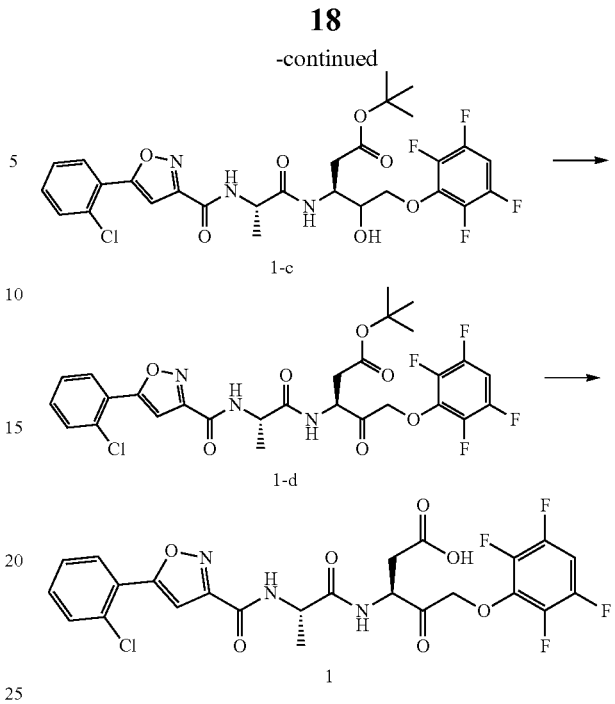

Step 1: Synthesis of Compound 1-c

Compound 1-b (100.00 mg, 447.21 μmol, 1.00 eq) was dissolved in dichloromethane (10.00 mL), and compound NMM (135.71 mg, 1.34 mmol, 147.51 μL, 3.00 eq), HOBt (82.78 mg, 612.67 μmol, 1.37 eq), EDCl (117.45 mg, 612.67 μmol, 1.37 eq) and compound 1-a (189.79 mg, 447.21 μmol, 1.00 eq) were added thereto. The reaction solution was stirred at 25° C. for 4 hours. After the reaction was completed, the reaction solution was directly concentrated to give a crude product, which was purified by flash silica-gel column chromatography (petroleum ether:ethyl acetate=4:1) to give a colorless oily compound 1-c. LCMS m/z=652.3 [M+Na]$^+$.

Step 2: Synthesis of Compound 1-d

Compound 1-c (220.00 mg, 349.22 μmol, 1.00 eq) was dissolved in dichloromethane (10.00 mL), and iodobenzene diacetate (435.31 mg, 1.35 mmol, 3.87 eq) and TEMPO (54.92 mg, 349.22 μmol, 1.00 eq) were added thereto. The reaction solution was stirred at 25° C. for 15 hours. After the reaction was completed, dichloromethane (20 mL) was added to the reaction solution, and the solution was successively washed with water (20 mL), saturated sodium bicarbonate solution (20 mL) and saline (20 mL). The organic phase was dried over anhydrous Na$_2$SO$_4$, filtered and concentrated to give a crude product. The crude product was purified by flash silica-gel column chromatography (petroleum ether:ethyl acetate=7:3) to give a light yellow oily compound 1-d. LCMS m/z=650.1 [M+Na]⁺.

Step 3: Synthesis of Compound 1

Compound 1-d (210.00 mg, 334.41 μmol, 1.00 eq) was dissolved in dichloromethane (4.00 mL), and trifluoroacetic acid (1.54 g, 13.51 mmol, 1.00 mL, 40.39 eq) was added thereto. The reaction solution was stirred at 25° C. for 3 hours. After the reaction was completed, the reaction solution was concentrated to give a crude product. The crude product was purified by prep-HPLC (in the condition of trifluoroacetic acid), and freeze-dried to give compound 1. ¹H NMR (400 MHz, DMSO-$d_6$) δ 12.47 (br s, 1H), 9.01 (br s, 1H), 8.67 (br s, 1H), 7.96 (dd, J=2.26, 7.28 Hz, 1H), 7.72 (d, J=7.39 Hz, 1H), 7.48-7.65 (m, 3H), 7.38 (s, 1H), 5.02-5.42 (m, 2H), 4.62 (d, J=6.02 Hz, 1H), 4.40-4.54 (m, 1H), 2.73-2.85 (m, 1H), 2.52-2.65 (m, 1H), 1.37 (d, J=7.03 Hz, 3H); LCMS m/z=572.1 [M+H]⁺.

Examples 2-17: The Compounds of Examples 2-17 were Prepared by Referring to the Synthetic Route of Example 1 and Replacing Compound 1-b with Different Intermediate Acids

| Example | Structure of intermediate acid | Structural formula |
|---|---|---|
| Example 2 | | |
| Example 3 | | |
| Example 4 | | |
| Example 5 | | |
| Example 6 | | |
| Example 7 | | |

-continued
| Example | Structure of intermediate acid | Structural formula |
|---|---|---|
| Example 8 | 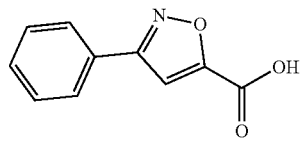 [SMILES: O=C(O)c1cc(-c2ccccc2)no1] | 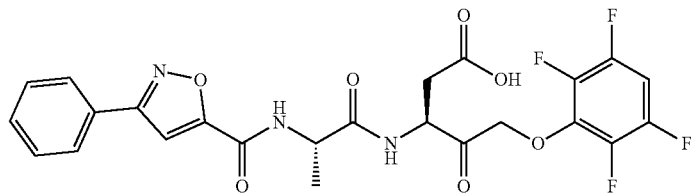 [SMILES: C[C@H](NC(=O)c1cc(-c2ccccc2)no1)C(=O)N[C@@H](CC(=O)O)C(=O)COc1c(F)c(F)cc(F)c1F] |
| Example 9 | 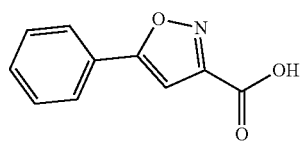 [SMILES: O=C(O)c1cc(-c2ccccc2)on1] | 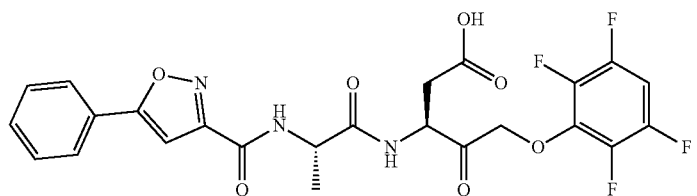 [SMILES: C[C@H](NC(=O)c1cc(-c2ccccc2)on1)C(=O)N[C@@H](CC(=O)O)C(=O)COc1c(F)c(F)cc(F)c1F] |
| Example 10 | 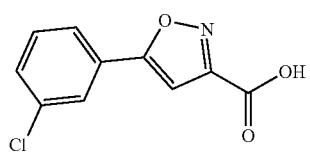 [SMILES: O=C(O)c1cc(-c2cccc(Cl)c2)on1] | 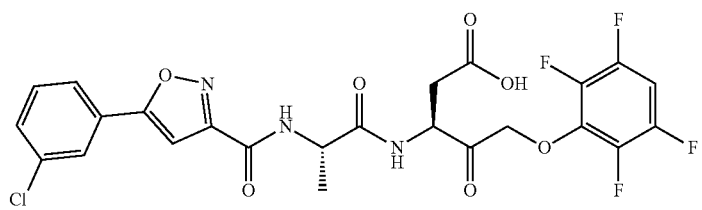 [SMILES: C[C@H](NC(=O)c1cc(-c2cccc(Cl)c2)on1)C(=O)N[C@@H](CC(=O)O)C(=O)COc1c(F)c(F)cc(F)c1F] |
| Example 11 | 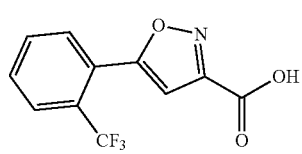 [SMILES: O=C(O)c1cc(-c2ccccc2C(F)(F)F)on1] | 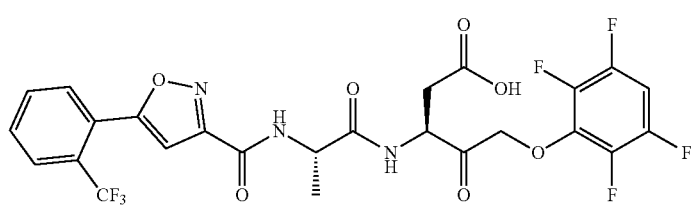 [SMILES: C[C@H](NC(=O)c1cc(-c2ccccc2C(F)(F)F)on1)C(=O)N[C@@H](CC(=O)O)C(=O)COc1c(F)c(F)cc(F)c1F] |
| Example 12 | 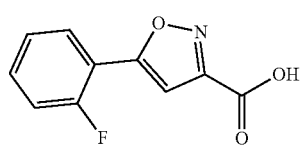 [SMILES: O=C(O)c1cc(-c2ccccc2F)on1] | 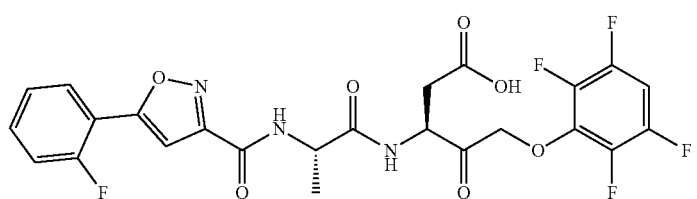 [SMILES: C[C@H](NC(=O)c1cc(-c2ccccc2F)on1)C(=O)N[C@@H](CC(=O)O)C(=O)COc1c(F)c(F)cc(F)c1F] |
| Example 13 | 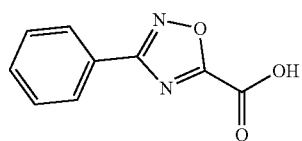 [SMILES: O=C(O)c1nc(-c2ccccc2)no1] | 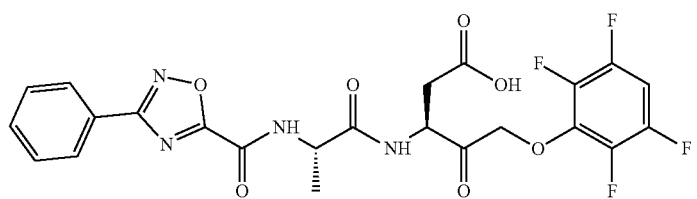 [SMILES: C[C@H](NC(=O)c1nc(-c2ccccc2)no1)C(=O)N[C@@H](CC(=O)O)C(=O)COc1c(F)c(F)cc(F)c1F] |
| Example 14 | 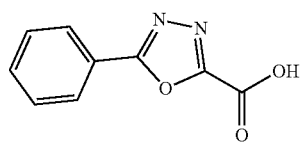 [SMILES: O=C(O)c1nnc(-c2ccccc2)o1] | 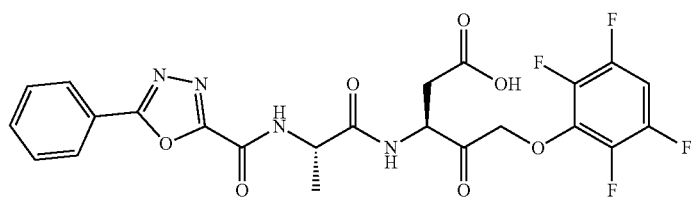 [SMILES: C[C@H](NC(=O)c1nnc(-c2ccccc2)o1)C(=O)N[C@@H](CC(=O)O)C(=O)COc1c(F)c(F)cc(F)c1F] |

| Example | Structure of intermediate acid | Structural formula |
|---|---|---|
| Example 15 | 2-chlorophenyl-1,2,4-oxadiazole-3-carboxylic acid | (corresponding amide product) |
| Example 16 | 5-cyclohexyl-isoxazole-3-carboxylic acid | (corresponding amide product) |
| Example 17 | 3-(2-chlorophenyl)-isoxazole-5-carboxylic acid | (corresponding amide product) |

Example 18: The Compound of Example 18 was Prepared by Referring to the Synthetic Route of Example 1 and Replacing Compound 1-a with Intermediate 1-e

| Example intermediate | Structural formula |
|---|---|
| Example 18 | (intermediate 1-e and final product structures) |

The NMR and MS data of Examples 2-13 and Examples 17-18 were as follows:

| Example | ¹H NMR | MS (m/z) [M + H]⁺ |
|---|---|---|
| Example 2 | ¹H NMR (400 MHz, DMSO-d$_6$) δ 8.82 (d, J = 7.03 Hz, 1H), 8.66 (br d, J = 7.78 Hz, 1H), 8.44 (s, 1H), 7.78 (br d, J = 7.28 Hz, 2H), 7.39-7.65 (m, 4H), 5.15-5.32 (m, 2H), 4.63 (q, J = 6.69 Hz, 1H), 4.45 (quin, J = 7.09 Hz, 1H), 2.75-2.83 (m, 1H), 2.58 (dd, J = 6.78, 16.81 Hz, 1H), 1.38 (d, J = 7.03 Hz, 3H) | 554.1 |
| Example 3 | ¹H NMR (400 MHz, DMSO-d$_6$) δ 8.70 (d, J = 7.53 Hz, 1H), 8.11 (brd, J = 5.52 Hz, 1H), 8.03 (d, J = 7.03 Hz, 2H), 7.85 (s, 1H), 7.40-7.60 (m, 4H), 5.15-5.35 (m, 2H), 4.59-4.70 (m, 1H), 4.48 (quin, J = 7.15 Hz, 1H), 2.73-2.83 (m, 1H), 2.60 (dd, J = 6.53, 17.07 Hz, 1H), 1.35 (d, J = 7.03 Hz, 3H) | 537.2 |

-continued

| Example | ¹H NMR | MS (m/z) [M + H]⁺ |
| --- | --- | --- |
| Example 4 | ¹H NMR (400 MHz, DMSO-d₆) δ 8.65 (d, J = 7.53 Hz, 1H), 7.80 (d, J = 7.03 Hz, 2H), 7.52-7.60 (m, 1H), 7.47 (br t, J = 7.53 Hz, 2H), 7.33-7.40 (m, 1H), 5.14-5.35 (m, 2H), 4.64 (q, J = 6.53 Hz, 1H), 4.46 (t, J = 7.03 Hz, 1H), 2.73-2.83 (m, 1H), 2.59 (dd, J = 6.53, 17.07 Hz, 1H), 1.35 (d, J = 7.03 Hz, 3H) | 537.1 |
| Example 5 | ¹H NMR (400 MHz, DMSO-d₆) δ 13.64-13.96 (m, 1H), 8.64 (d, J = 5.52 Hz, 1H), 7.81-8.31 (m, 2H), 7.21-7.66 (m, 6H), 5.13-5.35 (m, 2H), 4.63 (d, J = 5.02 Hz, 1H), 4.42-4.51 (m, 1H), 2.78 (dd, J = 5.77, 16.81 Hz, 1H), 2.54-2.65 (m, 1H), 1.35 (d, J = 7.03 Hz, 3H) | 555.1 |
| Example 6 | ¹H NMR (400 MHz, DMSO-d₆) δ 12.49 (br s, 1H), 8.91 (d, J = 6.52 Hz, 1H), 8.66 (d, J = 7.53 Hz, 1H), 7.97 (d, J = 8.53 Hz, 2H), 7.65 (d, J = 8.53 Hz, 2H), 7.50-7.62 (m, 1H), 7.43 (s, 1H), 5.17-5.32 (m, 2H), 4.62 (q, J = 6.53 Hz, 1H), 4.46 (quin, J = 7.03 Hz, 1H), 2.80 (dd, J = 6.02, 17.07 Hz, 1H), 2.59 (dd, J = 6.53, 17.07 Hz, 1H), 1.36 (d, J = 7.53 Hz, 3H) | 571.9 |
| Example 7 | ¹H NMR (400 MHz, DMSO-d₆) δ 12.49 (br s, 1H), 8.75 (s, 1H), 8.70 (d, J = 7.53 Hz, 1H), 8.26 (d, J = 6.53 Hz, 1H), 8.01-8.09 (m, 2H), 7.48-7.69 (m, 4H), 5.25 (q, J = 17.73 Hz, 2H), 4.65 (d, J = 6.53 Hz, 1H), 4.45-4.58 (m, 1H), 2.73-2.85 (m, 1H), 2.61 (dd, J = 6.02, 16.56 Hz, 1H), 1.38 (d, J = 7.03 Hz, 3H) | 538.0 |
| Example 8 | ¹H NMR (400 MHz, DMSO-d₆) δ 12.49 (br s, 1H), 9.17 (br s, 1H), 8.68 (br s, 1H), 7.93 (dd, J = 3.01, 6.53 Hz, 2H), 7.69 (s, 1H), 7.48-7.63 (m, 4H), 5.09-5.44 (m, 2H), 4.62 (d, J = 4.52 Hz, 1H), 4.39-4.53 (m, 1H), 2.80 (dd, J = 6.02, 16.06 Hz, 1H), 2.59 (d, J = 3.51 Hz, 1H), 1.37 (d, J = 7.03 Hz, 3H) | 538.0 |
| Example 9 | ¹H NMR (400 MHz, DMSO-d₆) δ 12.47 (br s, 1H), 8.89 (br s, 1H), 8.68 (br s, 1H), 7.89-7.98 (m, 2H), 7.50-7.65 (m, 4H), 7.38 (s, 1H), 5.12-5.40 (m, 2H), 4.63 (br s, 1H), 4.41-4.54 (m, 1H), 2.79 (dd, J = 6.53, 15.56 Hz, 1H), 2.61 (d, J = 4.02 Hz, 1H), 1.37 (d, J = 7.03 Hz, 3H) | 538.0 |
| Example 10 | ¹H NMR (400 MHz, DMSO-d₆) δ 12.46 (br s, 1H), 8.91 (br s, 1H), 8.65 (br s, 1H), 8.04 (s, 1H), 7.86-7.96 (m, 1H), 7.53-7.67 (m, 3H), 7.51 (s, 1H), 5.22 (br s, 2H), 4.64 (br s, 1H), 4.37-4.55 (m, 1H), 2.78 (dd, J = 5.52, 15.56 Hz, 1H), 2.55-2.66 (m, 1H), 1.37 (d, J = 7.03 Hz, 3H) | 572.0 |
| Example 11 | ¹H NMR (400 MHz, DMSO-d₆) δ 12.31 (br s, 1H), 8.97-9.08 (m, 1H), 8.69 (dd, J = 7.78, 15.81 Hz, 1H), 8.01 (d, J = 7.53 Hz, 1H), 7.89 (s, 2H), 7.80-7.87 (m, 1H), 7.49-7.67 (m, 1H), 7.16 (s, 1H), 5.13-5.39 (m, 2H), 4.64 (dt, J = 7.03, 13.55 Hz, 1H), 4.41-4.51 (m, 1H), 2.71-2.86 (m, 1H), 2.55-2.66 (m, 1H), 1.37 (d, J = 7.03 Hz, 3H) | 605.9 |
| Example 12 | ¹H NMR (400 MHz, DMSO-d₆) δ 12.48 (br s, 1H), 9.01 (br s, 1H), 8.69 (br s, 1H), 8.01 (t, J = 7.03 Hz, 1H), 7.38-7.77 (m, 4H), 7.22 (d, J = 2.51 Hz, 1H), 5.11-5.37 (m, 2H), 4.63 (br s, 1H), 4.40-4.53 (m, 1H), 2.79 (dd, J = 5.52, 16.56 Hz, 1H), 2.56-2.65 (m, 1H), 1.37 (d, J = 7.53 Hz, 3H) | 556.0 |
| Example 13 | ¹H NMR (400 MHz, DMSO-d₆) δ 9.60 (br s, 1H), 8.70 (br s, 1H), 8.09 (dd, J = 1.25, 7.78 Hz, 2H), 7.49-7.72 (m, 4H), 5.23 (br s, 2H), 4.40-4.74 (m, 2H), 2.79 (dd, J = 6.02, 16.31 Hz, 1H), 2.53-2.63 (m, 1H), 1.40 (d, J = 7.03 Hz, 3H) | 539.0 |
| Example 17 | ¹H NMR (400 MHz, DMSO-d₆) δ 9.22 (br d, J = 6.27 Hz, 1H), 8.67 (br s, 1H), 7.75 (dd, J = 1.51, 7.53 Hz, 1H), 7.68 (dd, J = 1.00, 7.78 Hz, 1H), 7.48-7.63 (m, 4H), 5.20 (br s, 2H), 4.65 (br s, 1H), 4.38-4.51 (m, 1H), 2.70-2.85 (m, 1H), 2.55-2.69 (m, 1H), 1.36 (d, J = 7.28 Hz, 3H). | 572.1 |
| Example 18 | ¹H NMR (400 MHz, DMSO-d₆) δ 12.47 (br s, 1H), 8.85-9.04 (m, 1H), 8.60-8.70 (m, 1H), 7.89-7.99 (m, 1H), 7.71 (d, J = 7.41 Hz, 1H), 7.48-7.64 (m, 3H), 7.34-7.40 (m, 1H), 5.12-5.38 (m, 2H), 4.51-4.69 (m, 1H), 4.31-4.50 (m, 1H), 2.72-2.85 (m, 1H), 2.53-2.66 (m, 1H), 1.37 (d, J = 7.03 Hz, 3H). | 572.0 |

Experimental Example 1: Assay of In Vitro Inhibitory Activity of Compounds on Caspase Experimental Purpose:

Caspase Inhibitor Screening Kit for BioVision was used in this experiment to test the inhibitory activity of the test compounds on Caspase.

Experimental Material:

1) Kit:

Caspase-1 Inhibitor Screening Kit (BioVision #K151-100)

Caspase-3 Inhibitor Screening Kit (BioVision #K153-100)

Caspase-8 Inhibitor Screening Kit (BioVision #K158-100)

Note: Each caspase enzymatic experiment uses the reagents in corresponding kit thereof. Each enzyme was dissolved in 550 µl of the corresponding 2× reaction buffer, sub-packed and stored at −80° C., respectively.

2) Black 384-well plate (PerkinElmer #6007279)

3) Instrument: Multi-function microplate reader Molecular Devices (Model: SpectraMax M2e)

Experimental Method:

1) The compound was diluted to a 200*test concentration with DMSO via the multiple dilution, then to a 2*test concentration with ddH$_2$O, and added to a 384-well experimental plate at 12.5 µl per well. Test compounds and control compounds were tested at 6 concentration points, test concentrations ranging from 1000 nM to 0.32 nM. The ddH$_2$O containing 1% DMSO was added to the 0% inhibition control well, and a high concentration of the control compound was added to the 100% inhibition control well (final concentration: 5 µM).

2) 2× reaction buffer containing 10 mM DTT was prepared. The enzyme caspase stock solution was diluted 5-fold with 2× reaction buffer containing 10 mM DTT and added to a 384-well experimental plate at 6.25 µl per well. After being mixed, the enzyme and compounds were incubated at 37° C. for 30 minutes.

3) The fluorogenic substrate of the enzyme caspase was diluted 5-fold with 2× reaction buffer containing 10 mM DTT, and then added to a 384-well experimental plate at 6.25 µl per well. The total reaction volume was 25 µl, the final concentration of the substrate was 50 µM, and the final concentration of DMSO was 0.5%. After the substrate was added, the 384-well experimental plate was incubated at 37° C. for 30 minutes.

4) The fluorescence intensity (excitation light wavelength was 400 nm, emission light wavelength was 505 nm) was measured by using a multi-function microplate reader. Fluorescence intensity was used to calculate the inhibitory effect of the compounds on Caspase. GraphPad Prism software was used for fitting compound inhibition curves and calculating IC$_{50}$ values.

Experimental Results:

The experimental results of the test compounds were shown in Table 1.

TABLE 1

Test results of enzymatic activities of test compounds

| Compound No. | Caspase-1 | Caspase-3 | Caspase-8 |
|---|---|---|---|
| Example 1 | 4.6 | 13.0 | 10.3 |
| Example 2 | 5.3 | 29.6 | 24.6 |
| Example 3 | 4.8 | 24.0 | 25.9 |
| Example 4 | 4.1 | 11.4 | 11.7 |
| Example 5 | 3.9 | 13.7 | 16.8 |
| Example 6 | 6.0 | 24.5 | 19.9 |
| Example 7 | 6.9 | 20.2 | 30.0 |
| Example 8 | 5.5 | 21.8 | 18.0 |
| Example 9 | 14.2 | 44.4 | 23.2 |
| Example 10 | 6.6 | 22.0 | 16.3 |
| Example 11 | 9.2 | 30.0 | 22.6 |
| Example 12 | 6.7 | 21.0 | 17.9 |
| Example 17 | 4.2 | 9.5 | 31.4 |
| Example 18 | 7.5 | 26.1 | 62.1 |

Experimental Conclusion:

As can be seen from the above Table 1, the compounds of the present application can have good inhibitory activity on Caspase.

Experimental Example 2: Mouse Pharmacokinetic Study

Experimental Purpose:

This experiment intended to investigate the pharmacokinetics in plasma and liver of male C57BL/6J mice after oral administration of the compounds.

Experimental Method:

Mice were randomly divided into three groups (3 male mice per group). The compound was formulated into the specified formulation. Oral formulations may be clear or uniform suspensions. Animals were intragastrically administered with a given dose of the preparation, respectively.

Whole blood samples were collected from animals through jugular vein puncture at 3 time points of 30 minutes, 2 hours, and 6 hours after administration, approximately 25 µL per sample; while the liver was collected at each time point.

The plasma samples were added to centrifuge tubes containing anticoagulant, and centrifuged at 4° C., 3000 g for 15 min, and the supernatant plasma was taken and quickly frozen on dry ice and then stored in a refrigerator at −70±10° C. until LC-MS/MS analysis was performed.

The blood outside the liver was sopped up with absorbent paper, and the weight of the liver was weighed, and then placed in liquid nitrogen to freeze. MeOH/15 mM PBS (1:2) at a volume-weight ratio of 1:5 was added thereto, and then the homogenization was performed at 14000 rpm for 2 minutes. It was then stored in a refrigerator at −70±10° C. until LC-MS/MS analysis was performed.

Data Processing:

The plasma drug concentration data for the compounds were processed with the non-compartment model using WinNonlin™ Version 6.3.0 (Pharsight, Mountain View, Calif.) pharmacokinetic software. The maximal concentration ($C_{max}$), maximal concentration time ($T_{max}$) and quantitative end time were directly obtained from the plasma concentration-time chart.

The following pharmacokinetic parameters were calculated by using logarithmic linear trapezoidal method: elimination phase half-life ($T_{1/2}$); the in vivo mean residence time of the drug from point 0 to the last time point (MRT$_{0-last}$); the in vivo mean residence time of the drug from point 0 to infinite time ($MRT_{0-ifn}$); the area under time-plasma concentration curve from point 0 to the last time point ($AUC_{0-last}$); the area under time-plasma concentration curve from point 0 to infinite time ($AUC_{0-inf}$).

For individual plasma concentrations less than BQL, the one occurred before $T_{max}$ was calculated as 0, and the one occurred after $T_{max}$ was directly excluded. All parameters and ratios were reported in the forms of three significant digits.

The pharmacokinetic parameters of this experiment were calculated according to the theoretical blood collection times and the theoretical administration concentrations in the protocol. The deviations between the actual administration concentrations and the theoretical concentrations were within the range of ±20%. The deviations between the actual blood collection times and the theoretical blood collection times were in conformity with the relevant SOP (the points within 1 hour after administration were within the range of ±1 min, and the others were within 5% of the theoretical time).

Experimental Results:

The experimental results of the test compounds were shown in Table 2.

TABLE 2

Pharmacokinetic study of the test compounds

| | Compound No. | IDN-6556 | Example 1 |
|---|---|---|---|
| 0.5 h | Plasma drug concentration (nM) | 435 | 2523 |
| | Liver drug concentration (nmol/kg) | 8600 | 46440 |
| 2 h | Plasma drug concentration (nM) | 10.9 | 112 |
| | Liver drug concentration (nmol/kg) | 930 | 3126 |
| 6 h | Plasma drug concentration (nM) | 5.79 | 12.8 |
| | Liver drug concentration (nmol/kg) | 230 | 3252 |
| | plasma drug-time curve (nM · h) | 314 | 1795 |
| | liver drug-time curve (nM · h) | 9347 | 48442 |
| | Area ratio of plasma/liver drug-time curves | 30 | 25 |

Experimental Conclusion:

It can be seen from the above Table 2 that, the reference compound IDN-6556 had a relatively small amount of liver exposure at different time points, and the area of the liver drug-curve was lower. The liver exposure of the compound shown in Example 1 can have significant improvement compared to IDN-6556, with about 5 times higher.

At the same time, Example 1 also maintained a comparable area ratio of liver/plasma drug-time curves. If drugs were used to treat liver diseases, high liver exposures of drugs make it possible for us to reduce the dose to be administered.

Experimental Example 3: Pharmacodynamic Study in Mice

Experimental Purpose:

The therapeutic effects of the test compound IDN-6556 and the compound of Example 1 in the $CCl_4$-induced chronic liver fibrosis model of male C57BL/6 mice were tested.

Experimental Method:

Male C57BL/6 mice were randomly divided into 7 groups: pseudo model group (group 1), model group (group 2, solvent p.o., q.d), IDN-6556 (group 3, 3 mg/kg, p.o., bid), IDN-6556 (group 4, 10 mg/kg, p.o., bid), Example 1 (group 5, 3 mg/kg, p.o., bid), Example 1 (group 6, 10 mg/kg, p.o., bid)), Example 1 (group 7, 20 mg/kg, p.o., bid). $CCl_4$ was formulated into a $CCl_4$-olive oil mixed solution according to the doses by using olive oil, modeling is performed by orally administration three times a week for 4 weeks; and the pseudo model group was orally administered with the same volume of olive oil alone. Compounds were orally administrated from the day of modeling, twice a day for 28 days, while the pseudo model group and the model group were orally administered with an equal volume of drug solvent. On the next day after the last administration, the animals were fasted for 6 hours, followed by euthanizing, and the livers were collected. Liver tissues were fixed in 10% formalin solution for histopathological analysis.

Experimental Results:

Table 3 showed pathology assay score of liver. It can be seen from this table that the different dose groups of IND-6556 and Example 1 all can significantly improve liver tissue damage caused by $CCl_4$, and in addition, Example 1 also significantly inhibited the formation of liver fibrosis compared with the model group ($p<0.01$).

TABLE 3

Pathology assay of liver (mean ± sem)

| Group | Total score of liver injury | Inflammatory cell infiltration | Ballooning change score | Percentage of liver fibrosis (%) |
|---|---|---|---|---|
| Group 1 | 0.00 ± 0.00 | 0.00 ± 0.00 | 0.00 ± 0.00 | 0.88 + 0.03 |
| Group 2 | 2.57 ± 0.29[###] | 2.00 + 1.20[###] | 0.50 + 0.14[###] | 1.95 + 0.09[###] |
| Group 3 | 1.60 ± 0.07*** | 1.55 + 0.06* | 0.05 + 0.04*** | 1.84 + 0.07 |
| Group 4 | 1.43 ± 0.12*** | 1.35 + 1.10*** | 0.08 + 0.04*** | 1.86 + 0.12 |
| Group 5 | 1.13 ± 0.06*** | 1.13 + 0.06*** | 0.00 ± 0.00*** | 1.61 + 0.05[$$] |
| Group 6 | 1.20 ± 0.07*** | 1.15 + 0.07*** | 0.00 ± 0.00*** | 1.62 + 0.07[$] |
| Group 7 | 1.12 ± 0.04*** | 1.10 + 0.04*** | 0.00 ± 0.00*** | 1.69 + 0.10 |

One-way ANOVA:

[###]$p < 0.001$ vs. group 1;

*$p < 0.05$ vs. group 2;

***$p < 0.001$ vs. group 2

T-test:

[$]$p < 0.05$ vs. group 2;

[$$]$p < 0.01$ vs. group 2.

Experimental Conclusion:

The results demonstrated that liver fibrosis of C57BL/6 mice was successfully induced by oral administration of $CCl_4$. Different doses of IDN-6556, oral administration twice a day for 28 days, can significantly inhibit $CCl_4$-induced liver tissue damage, especially inflammatory cell infiltration; however, no clear inhibitory effect on liver fibrosis was observed. Different doses of Example 1, oral administration twice a day for 28 days, can significantly inhibit $CCl_4$-induced liver tissue damage, particularly inflammatory cell infiltration, while significant inhibitory effect on liver fibrosis can be observed. Overall, the pharmacodynamic action of Example 1 was superior to IND-6556 in this model.

What is claimed is:

1. A compound represented by formula (I), a pharmaceutically acceptable salt or tautomer thereof,

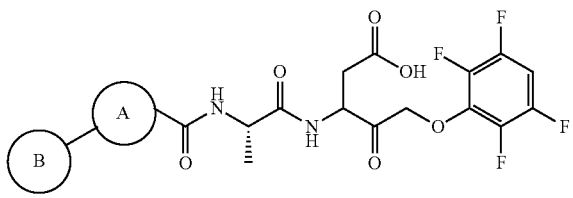

wherein,
ring A is selected from a 5- or 6-membered heteroaryl group, which is optionally substituted with R;
ring B is selected from phenyl or $C_{3-6}$ cycloalkyl, which is optionally substituted with R;
R is selected from halogen, OH, $NH_2$, or a $C_{1-3}$ alkyl group optionally substituted with 1, 2 or 3 $R^1$;
$R^1$ is selected from F, Cl, Br, I, OH, $NH_2$, $NH(CH_3)$ or $N(CH_3)_2$.

2. The compound, the pharmaceutically acceptable salt or tautomer thereof according to claim 1, wherein a heteroatom of ring A is independently selected from O, S or N, and number of the heteroatom of ring A is selected from 1, 2 or 3.

3. The compound, the pharmaceutically acceptable salt or tautomer thereof according to claim 1, wherein ring A is selected from oxazolyl, isoxazolyl, imidazolyl, thiazolyl, 1,2,4-oxadiazolyl, 1,3,4-oxadiazolyl or pyrazolyl.

4. The compound, the pharmaceutically acceptable salt or tautomer thereof according to claim 1, wherein ring A is selected from

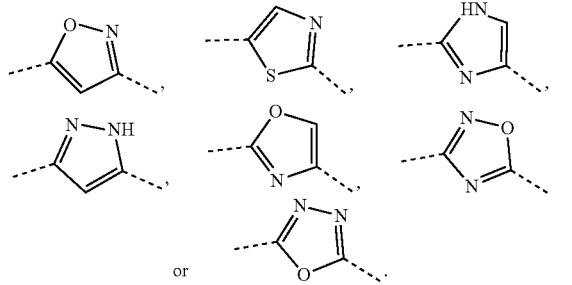

5. The compound, the pharmaceutically acceptable salt or tautomer thereof according to claim 1, wherein ring B is selected from phenyl or cyclohexyl, which is optionally substituted with R.

6. The compound, the pharmaceutically acceptable salt or tautomer thereof according to claim 1, wherein R is selected from F, Cl, Br, I, OH, $NH_2$, or Me or Et optionally substituted with 1, 2 or 3 $R^1$.

7. The compound, the pharmaceutically acceptable salt or tautomer thereof according to claim 6, wherein R is selected from F, Cl, Br, I, OH, $NH_2$ or $CF_3$.

8. The compound, the pharmaceutically acceptable salt or tautomer thereof according to claim 1, wherein ring B is selected from

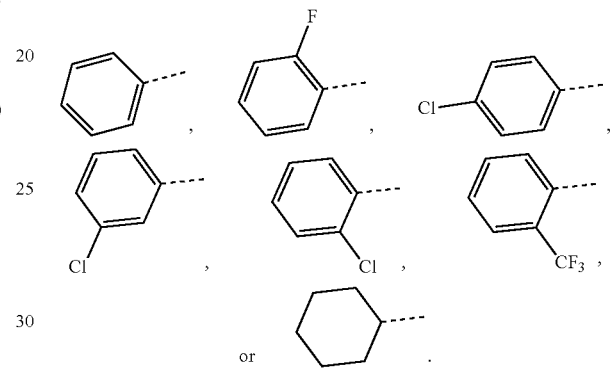

9. The compound, the pharmaceutically acceptable salt or tautomer thereof according to claim 1, wherein

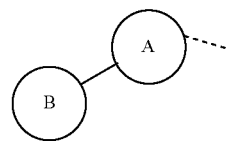

is selected from

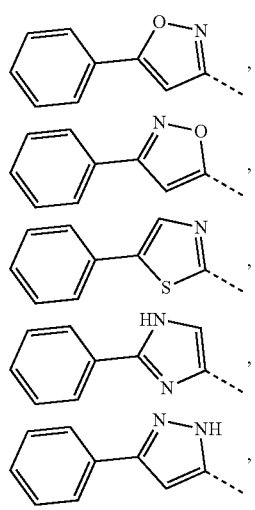

-continued

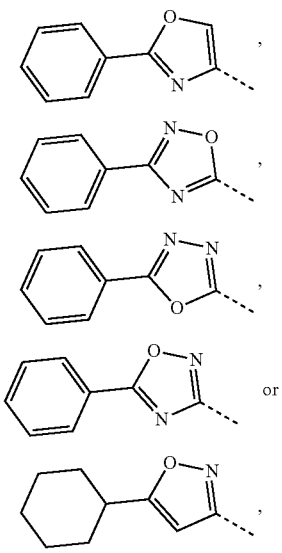

and ring B is optionally substituted with R.

10. The compound the pharmaceutically acceptable salt or tautomer thereof according to claim 1, wherein

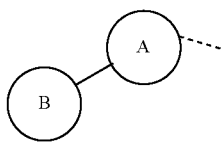

is selected from

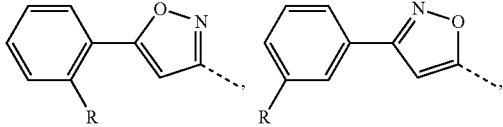

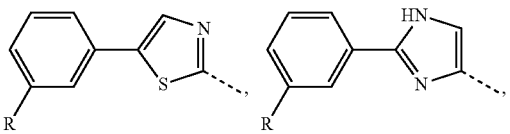

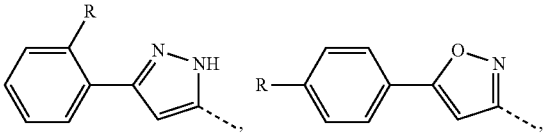

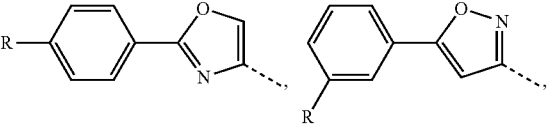

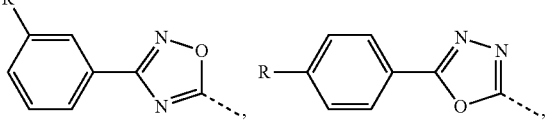

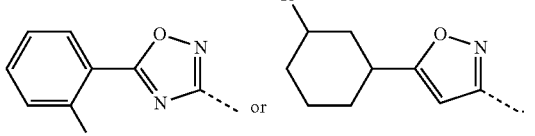

11. The compound, the pharmaceutically acceptable salt or tautomer thereof according to claim 10, wherein selected from 12. The compound, the pharmaceutically acceptable salt or tautomer thereof according to claim 1, wherein

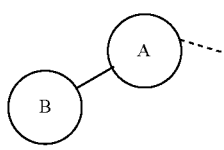
is selected from
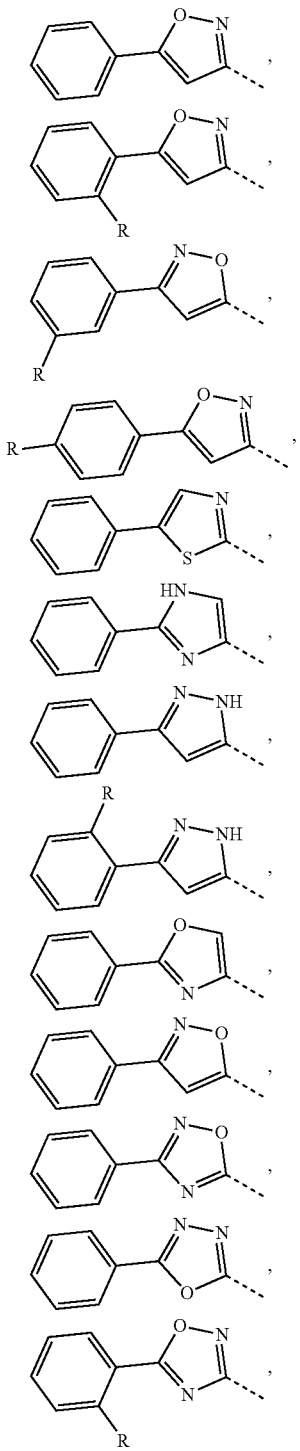
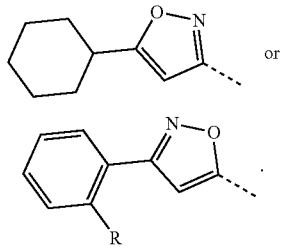 or
13. The compound, the pharmaceutically acceptable salt or tautomer thereof according to claim 1, wherein the compound is represented by the following formulae,
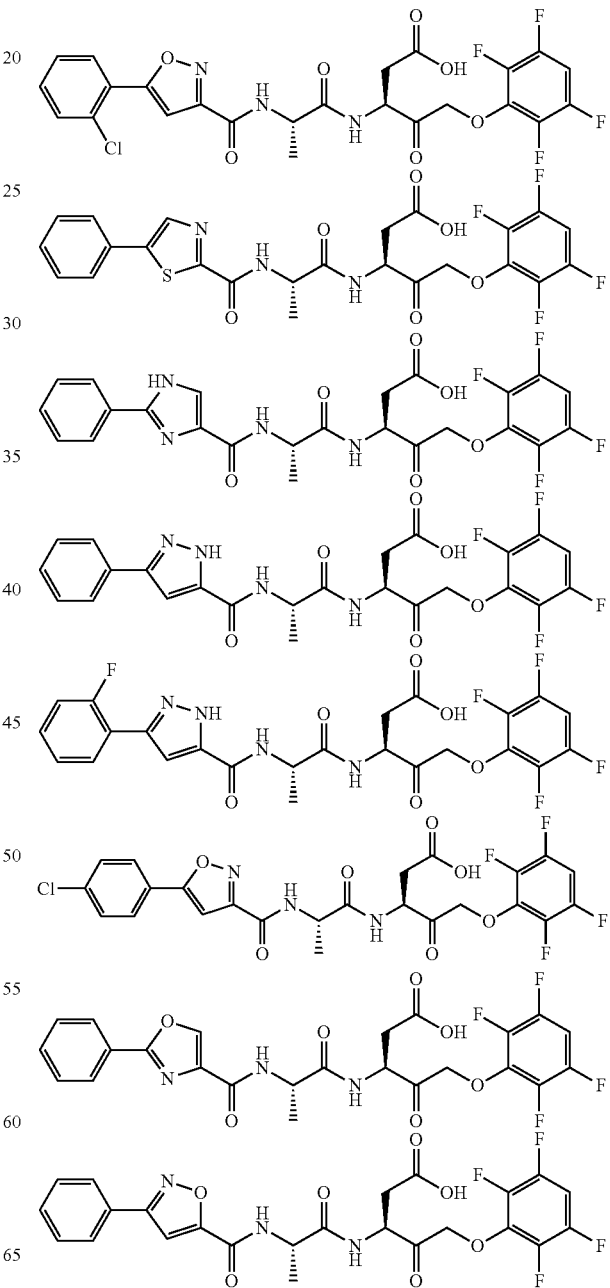

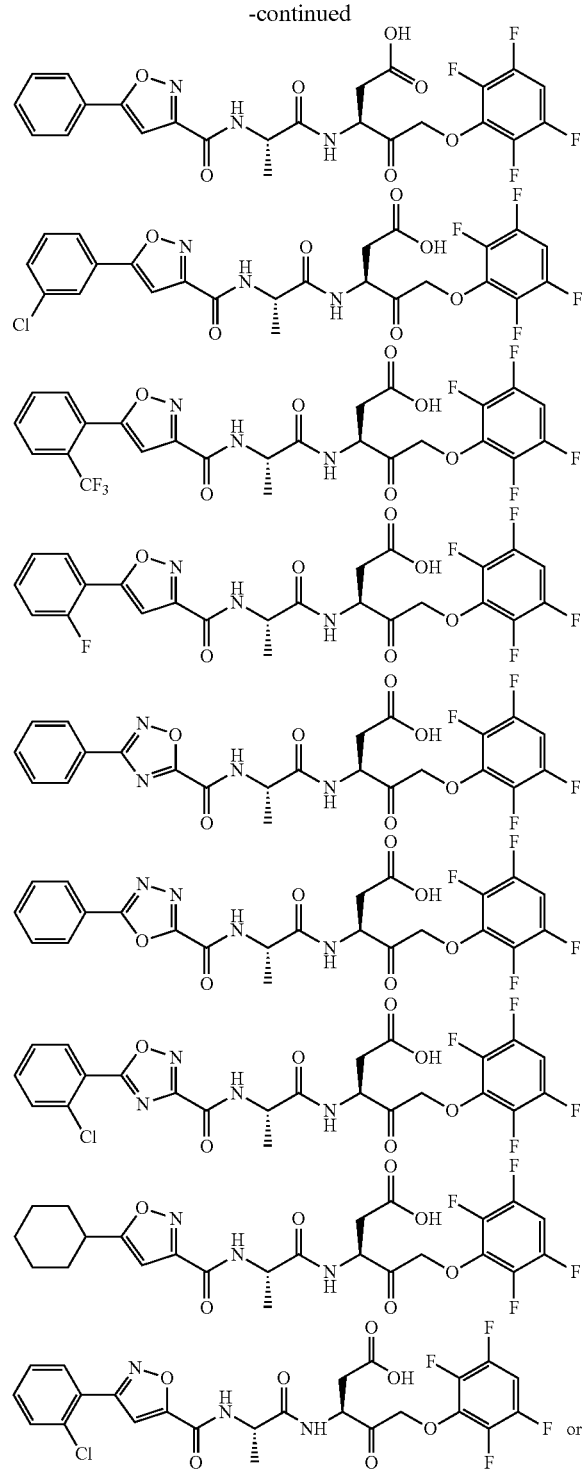

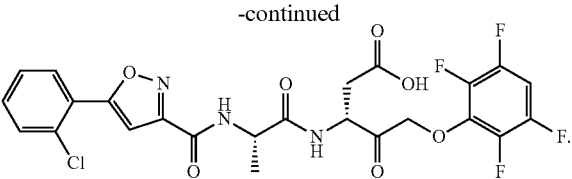

14. A pharmaceutical composition comprising a therapeutically effective amount of the compound, the pharmaceutically acceptable salt or tautomer thereof according to claim 1, and a pharmaceutically acceptable carrier or excipient.

15. A method of treating caspase receptor related diseases in a mammal, comprising administering a therapeutically effective amount of the compound, the pharmaceutically acceptable salt or tautomer thereof according to claim 1 to the mammal in need thereof.

16. The compound, the pharmaceutically acceptable salt or tautomer thereof according to claim 6, wherein R is selected from F, Cl, Br, I, OH, $NH_2$, or Me optionally substituted with 1, 2 or 3 $R^1$, and wherein $R^1$ is selected from F, Cl, Br or I.

17. The compound, the pharmaceutically acceptable salt or tautomer thereof according to claim 1, wherein R is selected from F, Cl, Br, I, OH, $NH_2$, or Me or Et optionally substituted with 1, 2 or 3 F.

18. The compound, the pharmaceutically acceptable salt or tautomer thereof according to claim 17, wherein R is selected from F, Cl, Br, I, or Me optionally substituted with 1, 2 or 3 F.

19. The compound, the pharmaceutically acceptable salt or tautomer thereof according to claim 7, wherein R is selected from F, Cl, Br, I or $CF_3$.

20. The compound, the pharmaceutically acceptable salt or tautomer thereof according to claim 1, wherein the compound is selected from a compound of formula (II),

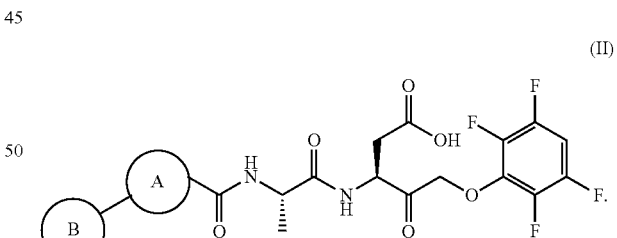

(II)

* * * * *